United States Patent [19]

Duff et al.

[11] Patent Number: 6,140,047
[45] Date of Patent: Oct. 31, 2000

[54] METHOD AND KIT FOR PREDICTING SUSCEPTIBILITY TO ASTHMA

[75] Inventors: Gordon W. Duff; Franco di Giovine; Peter Barnes; Samson Lim, all of Sheffield, United Kingdom

[73] Assignee: Interleukin Genetics, Inc., San Antonio, Tex.

[21] Appl. No.: 09/005,923

[22] Filed: Jan. 12, 1998

[30] Foreign Application Priority Data

Nov. 7, 1997 [GB] United Kingdom .................. 9723553

[51] Int. Cl.$^7$ .............................. C12Q 1/68; C12P 19/34; C07H 21/04
[52] U.S. Cl. ............................ 435/6; 435/91.2; 536/23.5; 536/24.31; 536/24.33
[58] Field of Search ...................... 435/6, 91.2; 536/23.5, 536/24.31, 24.33

[56] References Cited

U.S. PATENT DOCUMENTS

| | | | |
|---|---|---|---|
| 4,582,788 | 4/1986 | Erlich | 435/6 |
| 4,666,828 | 5/1987 | Gusella | 435/6 |
| 4,801,531 | 1/1989 | Frossard | 435/6 |
| 5,110,920 | 5/1992 | Erlich | 536/27 |
| 5,268,267 | 12/1993 | Smith | 435/6 |
| 5,674,483 | 10/1997 | Tu et al. | 424/85.2 |
| 5,686,246 | 11/1997 | Kornman et al. | 435/6 |

FOREIGN PATENT DOCUMENTS

| | | |
|---|---|---|
| WO 95/01997 | 1/1995 | WIPO . |
| WO 97/06180 | 2/1997 | WIPO . |
| WO 98/54359 | 12/1998 | WIPO . |

OTHER PUBLICATIONS

Pellegrino. Minerva Pediatrics. 48: 309–312, 1996.
McDowell, T. et al., "A Genetic Association Between Juvenile Rheumatiod Arthritis and a Novel Interleukin–1α Polymorphism", *Arthritis & Rheumatism*, 38:221–228 (1995).
Blakemore, et al., *J. Clin. Endocrinol.* 80(1): 111–5 (1995).
Blakemore, et al., *Hum. Genet.* 97(3): 369–74 (1996).
Blakemore, et al., *Arthritis Rheum.* 37: 1380–85 (1994).
Clark et al., *Nucleic Acids Res.* 14(20): 7897 (1986).
Clay, et al., *Hum. Genet.* 94: 407–10 (1994).
Cork, et al., *J. Invest. Dermatol.* 104(5 Supp.): 15S–16S (1995).
di Giovine, et al., *Cytokine* 7: 606 (1995).
di Giovine et al., "Single base polymorphism at –511 in the human interleukin–1β gene (IL1β)", *Human Molecular Genetics* 1(6) pp. Abstract only (1992).
Dinarello et al., "Anticytokine Strategies in the Treatmen of the Systemic Inflammatory Response Syndrome", *JAMA* 269:1829–1835 (1993).
Hiroyuki et al., "Classification of asthma based on genetics", *Japanese Journal of Thoracic Diseases* 33 (Supp):97–99 Abstract only (1995).
Hizawa et al., "Genetic analysis of bronchial asthma in Japanese population—Fc epsilon RI beta gene and beta 2 adrenergic receptor gene", *Japanese Journal of Clinical Medicine* 54(2):539–543 Abstract only (1996).
Kornman, et al., *J. Clin. Periodon.* 24;72 (1997).
Mansfield et al., "Novel Genetic Association Between Ulcerative Colitis and the Anti–Inflammatory Cytokine Interleukin–1 Receptor Antagonist", *Gastroenterology* 106: 637–642 (1994).
Marsh et al., "Genetic basis of IgE responsiveness: relevance to the atopic diseases", *International Archives of Allergy & Immunology* 107(1–3):25–28 Abstract only (1995).
Molvig, et al., *Scand. J. Immunol.* 27:705–16 (1988)).
Nicklin, et al., *Genomics* 19: 382–4 (1994).
Pociot, et al., *Eur J. Clin. Invest.* 22: 396–402 (1992).
Xu et al., "Evidence for two unlinked loci regulating total serum IgE levels", *American Journal of Human Genetics* 57(2):425–430 Abstract only (1995).
Zamel et al., "Asthma on Tristan de Cunha: looding for the genetic link", *American Journal of Respiratory & Critical Care Medicine* 153(6 Pt 1): 1902–1906 Abstract only (1996).

*Primary Examiner*—Carla J. Myers
*Attorney, Agent, or Firm*—Foley, Hoag & Eliot, LLP; Beth E. Arnold; Anita Varma

[57] ABSTRACT

The present invention provides a novel method for the early prediction of a propensity to develop chronic obstructive airway disorders such as asthma. The present invention also provides kits for the early determination of the propensity to develop such a disorder. The method consists of detecting the presence of one or more alleles of an IL-1B haplotype, specifically the IL-1b (+3954) and the IL-1B (–511) loci. The presence of allele 2 at the IL-1b (+3954) locus indicates increased risk for a chronic obstructive airway disorder. The presence of allele 2 at the IL-1B (–511) locus indicates susceptibility to more severe expression of chronic obstructive airway disorders.

15 Claims, No Drawings

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

CTCAGGTGTC CTCGAAGAAA TCAAA                                          25

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GCTTTTTTGC TGTGAGTCCC G                                              21

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TGGCATTGAT CTGGTTCATC                                                20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GTTTAGGAAT CTTCCCACTT                                                20

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
ACCTATCTTC TTCGACACAT GGGA                                              24

(2) INFORMATION FOR SEQ ID NO:6:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:6:

ACCTATCTTC TTTGACACAT GGGA                                              24

(2) INFORMATION FOR SEQ ID NO:7:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:7:

ATCCCATGTG TCGAAGAAGA TAGG                                              24

(2) INFORMATION FOR SEQ ID NO:8:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:8:

ATCCCATGTG TCAAAGAAGA TAGG                                              24

(2) INFORMATION FOR SEQ ID NO:9:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:9:

GAGAGCTCCC GAGGCAGAGA ACAG                                              24

(2) INFORMATION FOR SEQ ID NO:10:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:10:

GAGAGCTCCT GAGGCAGAGA ACAG                                              24
```

```
(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CTGTTCTCTG CCTCAGGAGC TCTC                                              24

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CTGTTCTCTA CCTCAGGAGC TCTC                                              24
```

METHOD AND KIT FOR PREDICTING SUSCEPTIBILITY TO ASTHMA

BACKGROUND

1. Field of the Invention

This invention relates to methods and kits for the identification of susceptibility to chronic obstructive airway diseases or disorders. Specifically, the method involves the detection of at least one allele in an IL-1B haplotype, such as an allele at the IL-1B (+3954) locus, which is indicative of an increased susceptibility to chronic obstructive airway disease such as asthma. Additionally, the method also involves the detection of an allele at the IL-1B (−511) locus, the presence of which is indicative of an increased susceptibility to severe asthma. Also included in the present invention are kits for the methods herein described.

2. Description of the Prior Art

Chronic obstructive lung disease and chronic obstructive airway disease (COAD) are broad terms used to describe not a disease entity, but rather a complex of conditions that have in common airflow limitation or airflow obstruction. COAD includes asthma, emphysema, chronic bronchitis, and chronic bronchiolitis. The sites of airway obstruction in COADs vary from the upper airways to the most peripheral bronchioles. The exact cause of most diseases of the airways is not well understood. The definition of airway diseases add to the confusion. Chronic bronchitis is defined clinically by the chronic presence of cough and sputum production. Emphysema, on the other hand, is defined anatomically, on the basis of the breakdown of lung tissue and the enlargement of the alveolar sacs. COADs all have airway narrowing as a disease parameter and they also share inflammation as a component of the disease process.

Asthma is a chronic lung disease characterized by coughing, chest tightness, shortness of breath, and wheezing due to a reversible obstruction of airflow resulting from inflammation and hyper-responsiveness of the airways. In sensitized individuals, inhalation of allergens may produce inflammation of the airway lining, and precipitate a flare-up of asthma. Asthma may also occur as a result of other inflammatory stimuli, such as respiratory tract infections. Individuals who have become sensitized to specific foods may have severely and possibly life-threatening reactions after ingestion of these substances. Asthma, once thought of as a "simple" hypersensitivity reaction, is now known to be a complex condition with a probable spectrum of causes and contributing factors, with airway inflammation as its central attribute. Pulmonary researchers liken it to arteriosclerosis, in the sense that there are many interactive aspects. Many of the contributing factors are now under intensive study, including the chemical reactions that take place in the asthmatic process; the nature of cell-cell communication, the way information is conveyed from one cell or type of cell to another; and the role, reactive or other, of the epithelium. Allergies contribute to both the incidence and severity of asthmatic symptoms. An allergy (also known as immediate hypersensitivity) is defined as an abnormal sensitivity to a substance which is normally tolerated and generally considered harmless, and for which the triggering event is dose-independent, as opposed to a dose-dependent idiosyncratic reaction to a substance. While all immune responses occur as a result of exposure to foreign substances, allergic reactions are distinct from the protective or enhanced "immunity" conferred by immunizations or natural infection. Only about a quarter of the children with asthma outgrow the condition when their airways reach adult size; for the rest, the condition is a lifelong ordeal. The condition persists, according to a research report published by the American Lung Association, in 85 percent of women and in 72 percent of men. (Journal of Allergy and Clinical Immunology Vol. 96:5 11/96).

There were 4,964 deaths from asthma recorded in 1993 in the United States of America. The incidence of asthma mortality in children doubled from 1980 to 1993. Among persons between the ages of 15 and 24 years, the number of deaths rose from 2.5 cases per million in 1980 to 5.2 cases per million in 1993. In 1993, asthma accounted for 342 deaths and approximately 198,000 hospitalization in persons under 25 years of age.

African-Americans account for 21 percent of deaths due to asthma. African-American children are four times more likely to die of asthma compared with Caucasian children. African-American males between the ages of 15 and 24 have the highest risk of mortality.

The mainstay of recognition of susceptibility and estimation of asthma is the family history and the patient's response to therapy. A positive family history tends to be one of the strongest risk factor associated with asthma. Positive identification though, can be difficult. Asthma may coexist with other conditions such as congenital abnormalities, infectious conditions, and cystic fibrosis. Additional indicators are considered when the history is atypical or the response to good medical management is poor. Physicians with less experience in the management of this disease may treat these symptoms as an infection, not realizing that the underlying cause is asthma.

The recognition of asthma severity in children relies heavily on the parents' observations for clinical clues. Correct identification requires an asthma and allergy specialist who recognizes the uniqueness of childhood asthma. More subtle signs of asthma, such as chest tightness, may be overlooked, or the child does not have the capability to properly identify the signs. Recurrent or constant coughing spells may be the only common observable symptoms of asthma in young children. Demonstration of a favorable clinical response to bronchodilator therapy can help confirm the presence of asthma.

There is a tremendous need for early identification of those who are generally susceptible to asthma. A susceptibility test which, from birth, can be used to screen for enhanced risk for a chronic obstructive airway disease would alert doctors to look for early signs of the disease, especially in children. Because it is a chronic and progressive disease when untreated, appropriate treatment could be administered at the earliest stage.

Advantages in positively identifying enhanced risk for asthma are apparent, especially regarding children. Early detection would reduce the costly, time-consuming process of elimination of factors that have routinely been used to identify enhanced risk of asthma.

Adults whose symptoms appear later in life, will benefit from a positive identification of increased susceptibility that allows the physician to treat them effectively without months of guesswork. Appropriate treatment and lifestyle changes can begin in an efficient manner, controlling the symptoms and keeping a positive check on the patient's needs. As disclosed herein, genetic testing can be used to make this important identification of increased susceptibility, and thereby make possible early intervention. The kind of treatment that a patient receives could also be influenced by a positive finding. Individuals are likely to be genetically predisposed to respond to some, but not all, treatment options. Identification of susceptibility to more severe disease by genetic testing of the IL-1 locus could be very useful in a clinical context, particularly for the prevention of severe asthma episodes by more aggressive therapy, and generally for clinical targeting of biomedical manipulation of the IL-1 system.

Genetic testing (also called genetic screening or genotyping) can be defined broadly as the testing of nucleic acid of a patient in an analytical capacity to determine if a patient contains mutations (or alleles or polymorphisms) that either cause or increase susceptibility to a disease state or are in "linkage disequilibrium" with the gene causing a disease state.

Linkage disequilibrium refers to the tendency of specific alleles to occur together more frequently than would be expected by chance. Alleles at given loci are in equilibrium if the frequency of any particular set of alleles (or haplotype) is the product of their individual population frequencies. The cause of disequilibrium is often unclear. It can be due to selection for certain allele combinations, or to a recent admixture of genetically heterogeneous populations. In addition, in the case of markers that very tightly link to a disease gene, an association of an allele (or a group of linked alleles) with the disease gene is expected if the disease mutation occurred in the recent past, so that sufficient time has not elapsed for equilibrium to be achieved through recombination events in that small chromosomal region.

The early detection of a predisposition to genetic diseases presents the best opportunity for medical intervention. Early genetic identification of risk may improve the prognosis for a patient through supervision and early intervention before the clinically detectable disorder occurs.

In cases where patients with similar symptoms are treated with variable success, sophisticated genetic testing can differentiate individual patients with subtle or undetectable differences and can lead to more suitable individual treatments. Early intervention may involve conventional pharmaceutical agents, non-pharmaceutical treatments and newer methods such as gene therapy or treatment with IL-1 modulators. With the development of genetic testing, it is now possible to identify gene mutations that indicate a propensity to develop disease, even when the disease is of polygenic origin. The number of diseases that can be identified by molecular biological methods continues to grow with increased understanding of the genetic basis of multifactorial disorders (see, e.g., U.S. Pat. Nos. 4,582,788; 5,110,920; 4,801,531; 4,666,828; and 5,268,267).

The IL-1 gene cluster is located on the long arm of human chromosome 2 (2q13) and contains at least the genes for IL-1 (IL1A), IL-1 (IL1B), and the IL-1 receptor antagonist (IL1RN) within a region of 430 Kb (Nicklin, et al., *Genomics* 19: 382–4 (1994)). The agonist molecules, IL-1 and IL-1, have potent pro-inflammatory activity and are at the head of many inflammatory cascades. Their actions, often via the induction of other cytokines such as IL-6 and IL-8, lead to activation and recruitment of leukocytes into damaged tissue, local production of vasoactive agents, fever response in the brain and the hepatic acute phase response. All three IL-1 molecules bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Inappropriate production of IL-1 appears to play a central role in the pathology of many autoimmune and inflammatory diseases, including rheumatoid arthritis, inflammatory bowel disorder, psoriasis, and others. In addition, there are stable inter-individual differences in the rates of production of IL-1, and some of this variation may be accounted for by genetic differences at IL-1 gene loci (Molvig, et at., *Scand. J. Immunol.* 27:705–16 (1988); Pociot, et al., *Eur. J. Clin. Invest.* 22: 396–402 (1992)).Thus, the IL-1 genes are reasonable candidates for determining part of the genetic susceptibility to inflammatory diseases such as chronic obstructive airway disease or asthma, most of which have a multifactorial etiology with a polygenic component.

Certain alleles from the IL-1 gene cluster are known to be associated with particular disease states. For example, IL1RN allele 2 is associated with coronary artery disease, osteoporosis, nephropathy in diabetes mellitus (Blakemore, et al., *Hum. Genet.* 97(3): 369–74 (1996)), alopecia areata (Cork, et al., *J. Invest. Dermatol.* 104(5 Supp.): 15S–16S (1995)), Graves disease (Blakemore, et al., *J. Clin. Endocrinol.* 80(1): 111–5 (1995)), systemic lupus erythematosus (Blakemore, et al., *Arthritis Rheum.* 37: 1380–85 (1994)), lichen sclerosus (Clay, et al., *Hum. Genet.* 94: 407–10 (1994)), and ulcerative colitis (Mansfield, et al., *Gastroenterol.* 106(3): 637–42 (1994)). The IL1B allele 2 from marker +3953 of IL-1B is also associated with psoriasis and insulin dependent diabetes in DR3/4 patients (di Giovine, et al., *Cytokine* 7: 606 (1995); Pociot, et al., *Eur J. Clin. Invest.* 22: 396–402 (1992)), and severe periodontal disease (Kornman, et al. *J. Clin. Periodon.* 24.72 (1997)).

However, in none of these studies or reports has there been described an association between asthma and other chronic obstructive airway diseases and the IL gene cluster such that one could identify increased susceptibility and/or monitor such diseases or disorders. These and other disadvantages of the prior art are overcome by the present invention.

SUMMARY OF THE INVENTION

The present invention provides a novel method for the early prediction of a propensity to develop chronic obstructive airway disorders such as, but not limited to asthma. It also provides kits for the early determination of the propensity to develop such a disorder.

The method of predicting increased risk for chronic obstructive airway diseases mediated by IL-1 biologic activity consists of detecting the presence of one or more alleles of an IL-1B haplotype. The polymorphism that is used to determine increased risk for chronic obstructive airway disease such as asthma is the IL-1B (+3954) locus. Having one or more of the alleles in an IL-1B haplotype indicates increased risk for a variety of chronic obstructive airway disorders. Also provided in the present invention is a method of predicting severity of a chronic obstructive airway disease such as asthma. The haplotype that is used to determine disease severity is the IL-1B (−511) locus. In those individuals who have a chronic obstructive airway disease, the presence of the rarer allele of the IL-1B (−511) locus indicates a greater risk for severe disease.

The identified pattern is compared to at least one control of known disease severity, thereby identifying patients with a genetic polymorphism pattern associated with increased risk of chronic obstructive airway disease severity. Patients so identified can then be treated more aggressively in the early stages of chronic obstructive airway disease to prevent or modulate the expression of severe disease. In another embodiment, the invention can be described as the following: isolating nucleic acid from the patient, identifying one or more alleles present in the IL-1B gene cluster, and comparing one or more of these alleles to a control sample. The control sample contains at least one allele from an IL-1 haplotype. Similarity of the identified alleles from the patient to the control sample indicates the patient's genetic predisposition to chronic obstructive airway disease.

Another embodiment of the invention is a kit for the detection of alleles that are predictive of chronic obstructive airway disease. The kit generally includes at least one oligonucleotide complementary to a DNA sequence in the IL-1B gene family and a control sample. The control sample contains an allele known to be associated with chronic obstructive airway disease, as described above. In one embodiment, provided is a kit for predicting a patient's increased risk of susceptibility to chronic obstructive airway disease, said kit comprising a DNA sample collecting means, a means for determining a genetic polymorphism pattern for an IL-1B; and control samples comprising polymorphic DNA sequences selected from the group consisting of IL-1B (+3954) allele 2 and IL-1B (−511) allele 2. The control sample may contain the actual PCR products produced by amplification of said alleles, or alternatively may contain genomic or cloned DNA from an individual that carries an IL-1B haplotype.

The kit may also include a DNA sampling means, a DNA purification means, and PCR reagents. Further, the oligonucleotide may contain a detectable label. The following oligonucleotides in their full length or in stretches longer than nine nucleotides, among others, may be present in the kit or used with the method:

5' CTC AGG TGT CCT CGA AGA AAT CAA A3' (SEQ ID No:1);

5' GCT TTT TTG CTG TGA GTC CCG 3' (SEQ ID No:2);

5' TGG CAT TGA TCT GGT TCA TC-3' (SEQ ID No:3);

5' GTT TAG GAA TCT TCC CAC TT-3' (SEQ ID No:4);

5' ACC TAT CTT CTT CGA CAC ATG GGA 3' (SEQ ID No:5);

5' ACC TAT CTT CTT TGA CAC ATG GGA 3' (SEQ ID No:6);

5' ATC CCA TGT GTC GAA GAA GAT AGG 3' (SEQ ID No:7);

5'ATC CCA TGT GTC AAA GAA GAT AGG 3' (SEQ ID No:8);

5' GAG AGC TCC CGA GGC AGA GAA CAG 3' (SEQ ID No:9);

5' GAG AGC TCC TGA GGC AGA GAA CAG 3' (SEQ ID No: 10);

5' CTG TTC TCT GCC TCA GGA GCT CTC 3' (SEQ ID No:11); and

5' CTG TTC TCT ACC TCA GGA GCT CTC 3' (SEQ ID No: 12).

Other embodiments and advantages of the invention are set forth in part in the Detailed Description which follows, and will be obvious from this description, or may be learned from the practice of the invention.

DETAILED DESCRIPTION

As embodied and broadly described herein, the present invention is directed to methods for the detection of at least one allele of an IL-1 haplotype, including the IL-1B haplotype, that is associated with chronic obstructive airway disease.

The term 'marker,' as used herein, refers to a specific site in the genome which exhibits sequence variations between individuals. For example, herein described is the marker IL-1B (+3954) for identification of propensity to develop or have a chronic obstructive airway disease such as asthma. Also described is the marker IL-1B (−-511) for identification of propensity to develop more severe forms of the disease.

The term 'allele' refers to the different sequence variants found at given markers. The sequence variants may be single or multiple base changes, including insertions, deletions or substitutions or may be variable number of sequence repeats and the like. Allelic variants at a certain locus are commonly numbered in decreasing order of frequency. In a biallelic situation the frequent allele is allele 1, the rarer allele will be allele 2.

The term 'linkage disequilibrium' refers to the co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in 'linkage equilibrium.'

The term 'haplotype' is a set of alleles that are inherited together as a group (are in linkage disequilibrium). As used herein, haplotype is defined to include those haplotypes that occur at statistically significant levels ($P_{corr}$ 0.05).

As used herein the phrase 'an IL-1 haplotype' refers to a haplotype in the IL-1 locus, It includes at least the IL-1B (+3954) marker as described herein, the presence of which indicates increased risk of developing a chronic obstructive airway disease such as asthma. Additionally, the presence of the rarer allele of the IL-1B (−511) marker indicates an increased risk of developing severe chronic obstructive airway disease with more severe symptoms that requires more specialized treatment.

The phrase 'chronic obstructive airway disease' or 'chronic obstructive airway disorder,' as used herein, refers to those diseases associated with inheritance of an IL-1B haplotype and which are a complex of conditions that have in common airflow limitation or airflow obstruction. The phrase includes asthma, emphysema, chronic bronchitis, and chronic bronchiolitis.

As used herein, the process of 'detecting alleles' is variously described as 'genotyping, determining or identifying an allele or polymorphism,' or any similar phrase. The allele actually detected might be a disease-causing mutation, or a mutation that is in linkage disequilibrium with a disease-causing mutation. It will be manifest in the genomic DNA of a patient, but may also be detectable from RNA or protein sequences transcribed or translated from this region.

By 'propensity,' 'predisposition' or 'susceptibility' to disease what is meant is that certain alleles are hereby discovered to be 'associated' with chronic airway obstructive disease. They are thus over represented in frequency in individuals with disease as compared to healthy individuals (for the rarer allele of the +3954 polymorphism) or over represented in frequency in individuals with severe disease (for the rarer allele of the −511 polymorphism). Consequently, the IL-1B (−511) genotype 1.1 is significantly more prevalent in those with mild disease compared to those with severe disease.

The invention is directed to a method of predicting the propensity or predisposition of a patient to chronic obstructive airway disease by genotyping the patient's DNA at the IL-1B gene cluster. The patient's genotype is compared with a control sample that contains one or more alleles from an IL-1B haplotype, such as but not limited to the IL-1B (+3954) marker and/or the IL-1B (−511) marker. DNA is extracted from a suitable specimen using techniques known to those skilled in the art. Suitable specimens are those which comprise cells and DNA and include, but are not limited to blood, buccal swabs and saliva.

Techniques for determining the presence or absence of the particular allele of interest may be nucleic acid techniques based on size or sequence, such as restriction fragment length polymorphism (RFLP), nucleic acid sequencing, or hybridization. These techniques may also comprise the step of amplifying the nucleic acid before analysis. Amplification techniques are known to those of skill in the art and include cloning, polymerase chain reaction (PCR), polymerase chain reaction of specific alleles (PASA), ligase chain reaction, nested polymerase chain reaction, and the like. Amplification products may be assayed in a variety of ways, including size analysis, restriction digestion followed by size analysis, detecting specific tagged oligonucleotide primers in the reaction products, allele-specific oligonucleotide (ASO) hybridization, sequencing, hybridization, and the like.

PCR based detection means include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be detected. Other techniques are known in the art to allow multiplex analyses of a plurality of markers.

The amplified DNA sequences from the template DNA are then analyzed using restriction enzymes to determine if the genetic polymorphism is present in the amplified sequences and thereby provides a genetic polymorphism profile of the patient. Allele detection techniques may include iucleic acid sequencing, hybridization and methods of allele detection or may be protein based if a particular allele produces a protein with an amino acid variant. For example, epitopes specific for the amino acid variant can be detected with monoclonal antibodies. Likewise, it is possible to detect alleles if they are present in processed RNA by techniques that are known in the art.

Another embodiment of the invention is directed to kits for detecting a propensity for enhanced risk of chronic obstructive airway disease in a patient. The kits can be used pre- or post-symptomatically or prenatally. The kit may comprise one or more oligonucleotide capable of hybridizing to nucleic acid from the IL-1B gene cluster. A number of assay formats are useful for genotyping using the provided oligonucleotide. The most common formats involve nucleic acid binding, such binding to filters, beads, or microtiter plates and the like. Techniques may include dot blots, RNA blots, DNA blots, PCR, RFLP, and the like.

The oligonucleotide may be a variety of natural and synthetic compositions such as synthetic oligonucleotide, restriction fragments, cDNAs, synthetic PNAs, and the like. The assay may also employ labeled oligonucleotide to allow ease of identification in the assays. Examples of labels which may be employed include radiolabels, enzymes, fluorescent compounds, streptavidin, avidin, biotin, magnetic moieties, metal binding moieties, antigen or antibody moieties, and the like. Oligonucleotides useful in the present invention for identifying the IL-1B (+3954) marker include an oligonucleotide selected from the group consisting of the following, or other oligonucleotides which include their sequence, in their full length or in stretches longer than nine nucleotides:

5' CTC AGG TGT CCT CGA AGA AAT CAA A 3' (SEQ ID No: 1);

5' GCT TTT TTG CTG TGA GTC CCG 3' (SEQ ID No:2);

5' ACC TAT CTT CTT CGA CAC ATG GGA 3' (SEQ ID No:5);

5' ACC TAT CTT CTT TGA CAC ATG GGA 3' (SEQ ID No:6);

5' ATC CCA TGT GTC GAA GAA GAT AGG 3' (SEQ ID No:7); and

5' ATC CCA TGT GTC AAA GAA GAT AGG 3' (SEQ ID No:8).

Oligonucleotides useful in the present invention for identifying the IL-1B (−511) marker include an oligonucleotide selected from the group consisting of the following, or other oligonucleotides which include their sequence, in their full length or in stretches longer than nine nucleotides:

5' TGG CAT TGA TCT GGT TCA TC-3' (SEQ ID No:3);

5' GTT TAG GAA TCT TCC CAC TT-3' (SEQ ID No:4);

5' GAG AGC TCC CGA GGC AGA GAA CAG 3' (SEQ ID No:9);

5' GAG AGC TCC TGA GGC AGA GAA CAG 3' (SEQ ID No: 10);

5' CTG TTC TCT GCC TCA GGA GCT CTC 3' (SEQ ID No: 11); and

5' CTG TTC TCT ACC TCA GGA GCT CTC 3' (SEQ ID No: 12).

The kit may also include DNA sampling means. The DNA sampling means is any means known to those skilled in the art such as, but not limited to filter paper that is suitable for collecting blood specimens that contain DNA. Useful filter papers include, but are not limited to Schleicher & Schuell Nos 2992 and 903 (Keene, N.H., USA). The kit may also comprise a DNA purification means such as a device or reagent for effecting cell lysis with SDS followed by proteinase K digestion, reagents such as 10× reaction buffers, thermostable polymerase, dNTPs, and the like. The DNA is then isolated from the specimen and target sequences amplified using an amplification technique. Oligonucleotide DNA primers that target the specific polymorphic DNA region within the genes of interest are prepared so that in the PCR reaction amplification of the target sequences is achieved. This embodiment has the advantage of requiring only a small amount of specimen and avoids the necessity for venipuncture or a tissue biopsy.

The following examples illustrate embodiments of the invention, but should not be viewed as limiting the scope of the invention.

EXAMPLES

Example 1

IL-1B Analysis

The screening of the single base variation (C/T) polymorphism at IL-1B base +3954 was conducted by PCR amplification of genomic templates. One mismatch was inserted in a primer to complete a TaqI site as a positive control. The polymorphic TaqI site is native. The following primers were produced in an ABI DNA synthesizer based on the genomic sequences (Clark et al., 1986; GENBANK X04500):

5' CTC AGG TGT CCT CGA AGA AAT CAA A 3' (SEQ ID No:1)

5' GCT TTT TTG CTG TGA GTC CCG 3' (SEQ ID No:2)

The PCR reaction conditions were as follows:

[95 C (2 minutes)] 1 cycle;

[95 C(1 minute), 67.5 C (1 minute), 74 C (1 minute)] 38 cycles; and

[72 C (8 minutes)] 1 cycle.

Restriction enzyme digestion was conducted at 60 C, for 8 hours. Sizing was by 8% PAGE. The digestion of the PCR product with Taq I yields a segment of 12 bp (the absence of which indicates incomplete digestion) and either two further segments of 85 and 97 bp (allele 1), or a single one of 182 bp (allele 2). This protocol provided efficient analysis of the IL-1B (+3954) locus.

The single base polymorphism (C/T) at position −511 in the IL-1B gene was screened by PCR amplification of genomic templates, followed by RFLP (Restriction Fragment Length Polymorphism) analysis. The gene variation completes an Ava I restriction site in the most frequent allele, and a Bsu 36 I site in the rarer allele. Hence digestion of the PCR product with these enzymes provides efficient analysis of the IL-1B (−511) locus.

The following primers were produced in an ABI synthesizer based on the genomic sequence (Clark et al, 1986; Genbank X04500).

5' TGG CAT TGA TCT GGT TCA TC-3' (SEQ ID No:3)
5' GTT TAG GAA TCT TCC CAC TT-3' (SEQ ID No:4)
PCR conditions were as follows:
[95 C (1 minute)] 1 cycle
[95 C (1 minute)] 53 C (1 minute), 72 (1 minute)] 35 cycles
[72 C (5 minute)] 1 cycle Each PCR reaction was divided in two 25 ul aliquots; one was added to 3 units of Ava I, the other to 3.7 units of Bsu 36 I, in addition to 3 ul of the specific 10× restriction buffer. Digestion was at 37 C overnight, sizing was by 9% PAGE. Ava I digestion produced 190+114 bp segments with allele 1, while allele 2 was uncut (304 bp). The Bsu 36 I digestion produced 190+114 bp fragments with allele 2, while allele 1 was uncut (304 bp). The restriction pattern obtained was inverted in the two aliquots (identifying homozygotes) or identical (identifying heterozygotes).This protocol provided efficient analysis of the IL-1B(−511) locus.

steroids (FEV1 58.4+3.4% pred) with a mean age of 47.2+ 2.3 Informed consent was obtained and then 10 mls of venous blood was drawn and collected in EDTA-containing tubes from each patent. Total genomic DNA was extracted and allele frequencies were assessed in DNA extracted from the 106 patients. For IL-1B (+3954) 105 patients could be genotyped. 104 patients were genotyped for IL-1B (−511). For each DNA, a single PCR product spanning the relevant regions of the IL-1 B gene was produced and analyzed as described in Example 1. The data were analyzed using the Chi square test to compare carriage of the rare allele (genotypes carrying at least one copy of allele 2 between cohorts) as detailed below.

The presence of the (+3954) allele 2 was significantly associated with clinical disease as shown in Table 1.

TABLE 1

| | IL-1B (+3953) | | |
|---|---|---|---|
| Disease Severity | 1.1 | 1.2 | 2.2 |
| MILD (N = 50) | 28 | 17 | 5 |
| SEVERE (N = 55) | 26 | 24 | 5 |
| CONTROLS (N = 251) | 165 | 81 | 5 |
| Mild vs Severe | $Chi^2$ = 0.497 | p = 0.48 | (N.S.) |
| "all" vs Control | $Chi^2$ = 6.402 | p =0.01 | O.R. = 1.81 (95% C.I. = 1.14–2.88) |
| Severe vs Control | $Chi^2$ = 6.557 | p =0.01 | O.R. = 2.14 (95% C.I. = 1.19–3.86) |

Example 2

Effectiveness of Markers in Detecting Propensity of Disease.

This example demonstrates the effectiveness of the IL-1B (+3954) marker in predicting propensity for developing asthma and of the IL-1B (−511) locus in predicting disease severity. The following study was conducted to evaluate whether there was an association between asthma and alleles found in the relevant regions of the IL-1B gene. One hundred six (106) asthma patients were recruited for the study. 251 North British white Caucasian non-asthmatic subjects were recruited as controls. All asthma patients fulfilled the ATS criteria for the definition of asthma (Amer Rev Respir Dis 1985, 132:180–182.), and where relevant had a PC20 methacholine of less than 4 mg/ml. Asthma patients were clinically categorized as having either mild or severe asthma. Severe asthma was defined as those patients requiring more than 800mg/day of inhaled steroids. Asthma patients on beta-2 agonist alone were categorized as having mild asthma. Of the total number of asthma patients, 50 were mild asthmatics on beta 2 agonist alone (FEV1 92.5±1.5% pred) and had a mean age of 26.5±0.9, and 56 were severe asthmatics on a regimen of at least 800 mg per day of inhaled In conclusion, the presence of the IL-1B (+3954 )allele 2 showed a statistically significant association with asthma, demonstrating that it can be used to predict a patient's susceptibility to a chronic obstructive airway disease such as asthma.

In contrast, the presence of the (−511) allele 2 is useful for identifying an individual's risk of developing or having severe asthma. Data were analyzed using the Chi square test to compare carriage of the rare allele (genotypes carrying at least one copy of allele 2) between cohorts as detailed below. This is shown in Table 2.

TABLE 2

| | IL-1B (−511) | | |
|---|---|---|---|
| Disease Severity | 1.1 | 1.2 | 2.2 |
| MILD (N = 50) | 28 | 19 | 3 |
| SEVERE (N = 54) | 19 | 31 | 4 |
| CONTROLS (N = 25.1) | 89 | 129 | 33 |
| Severe vs Mild | $Chi^2$ = 4.541 | p = 0.033 | O.R. = 2.34 (95% C.I. = 1.06–5.16) |
| "all" vs Control | $Chi^2$ = 2.948 | p = 0.086 | (NS) |

In subjects with a clinical diagnosis of asthma, the presence of allele 2 at the IL-1B (−511) locus (i.e. genotype 1.1) is associated with more severe disease. This is shown in Table 2, in which the IL-1B (−511) genotype 1.1 is more prevalent in those with mild disease compared to those with severe disease, and conversely genotypes carrying at least one copy of allele 2 are more frequent in the cohort of patients with more severe disease.

What is claimed is:

1. A kit comprising:
   (a) DNA sample collecting means;
   (b) means for determining a genetic polymorphism pattern for IL-1B wherein said means comprises a set of polymerase chain reaction (PCR) primers, wherein said PCR primers are selected from the group consisting of:
   5' ACC TAT CTT CTT CGA CAC ATG GGA 3' (SEQ ID No:5);
   5' ACC TAT CTT CTT TGA CAC ATG GGA 3' (SEQ ID No:6);
   5' ATC CCA TGT GTC GAA GAA GAT AGG 3' (SEQ ID No:7);
   5' ATC CCA TGT GTC AAA GAA GAT AGG 3' (SEQ ID No:8);
   5' GAG AGC TCC CGA GGC AGA GAA CAG 3' (SEQ ID No:9);
   5' GAG AGC TCC TGA GGC AGA GAA CAG 3' (SEQ ID No:10);
   5' CTG TTC TCT GCC TCA GGA GCT CTC 3' (SEQ ID No: 11); and
   5' CTG TTC TCT ACC TCA GGA GCT CTC 3' (SEQ ID No:12); and
   (c) control samples comprising polymorphic DNA sequences selected from the group consisting of IL-1B (+3954) allele 2 and IL-1B (−511) allele 2.

2. The kit as set forth in claim 1, wherein the means for determining the genetic polymorphism pattern further comprises a restriction enzyme selected from the group consisting of Taq I, Ava I and Bsu36 I.

3. A method of predicting a patient's increased risk of susceptibility to asthma, comprising the steps of:
   (a) isolating genomic DNA from a patient;
   (b) identifying a genetic polymorphism pattern for IL-1B in the genomic DNA; and
   (c) comparing the genetic polymorphism pattern to a control sample
   wherein the control sample comprises at least one IL-1B allele selected from the group consisting of a polymorphism at IL-1B (+3954) locus and a polymorphism at IL-1B(−511) locus, which polymorphisms are known to be associated with chronic obstructive airway disease; and
   wherein when the genetic polymorphism pattern of the patient is identical to the genetic polymorphism pattern of the control sample, the patient has an increased risk of susceptibility to asthma.

4. The method as set forth in claim 3, wherein the control sample comprises a specimen having the polymorphic sequence of an IL-1B (+3954) allele.

5. The method as set forth in claim 3, wherein the control sample comprises a specimen having the polymorphic sequence of an IL-1B (−511) allele.

6. The method as set forth in claim 3, wherein the allele known to be associated with the increased risk of asthma comprises the polymorphic sequence of an IL-1B (+3954) allele.

7. The method set forth in claim 3, wherein the allele known to be associated with the increased risk of chronic obstructive airway disease comprises the polymorphic sequence of an IL-1B (−511) allele.

8. The method as set forth in claim 7 wherein the presence of said IL-1B (−511) is indicative of an increased propensity for severe asthma.

9. A method of predicting a patient's increased risk of susceptibility to asthma, said method comprising the steps of:
   (a) isolating genomic DNA from a patient;
   (b) determining an allelic pattern for IL-1B in the genomic DNA;
   wherein the allelic pattern selected from the group consisting of at least one copy of the polymorphic sequence of the IL-1B (+3954) allele, indicates increased risk of susceptibility to asthma.

10. The method as in claim 9, wherein said step of determining an allelic pattern comprises amplification with a polymerase chain reaction (PCR) and at least one PCR primer, wherein said PCR primer is selected from the group consisting of:
   5' CTC AGG TGT CCT CGA AGA AAT CAA A3' (SEQ ID No:1); and 5' GCT TTT TTG CTG TGA GTC CCG 3' (SEQ ID No:2).

11. The method as in claim 9, wherein said step of determining an allelic pattern comprises digestion with a Taq I restriction enzyme.

12. A method of predicting a patient's increased risk of susceptibility to severe asthma, said method comprising the steps of:

(a) isolating genomic DNA from a patient;

(b) determining an allelic pattern for IL-1B in the genomic DNA;

wherein the absence of an allelic pattern selected from the group consisting of at least one copy of the polymorphic sequence of an IL-1B (−511) allele indicates increased risk of susceptibility to severe asthma.

13. The method as in claim 12, wherein said step of determining an allelic pattern comprises amplification with a polymerase chain reaction (PCR) and at least one PCR primer, wherein said PCR primer is selected from the group consisting of:

5' TGG CAT TGA TCT GGT TCA TC-3' (SEQ ID No:3);

5' GTT TAG GAA TCT TCC CAC TT-3' (SEQ ID No:4);

5' ACC TAT CTT CTT CGA CAC ATG GGA 3' (SEQ ID No:5);

5' ACC TAT CTT CTT TGA CAC ATG GGA 3' (SEQ ID No:6);

5' ATC CCA TGT GTC GAA GAA GAT AGG 3' (SEQ ID No:7);

5' ATC CCA TGT GTC AAA GAA GAT AGG 3' (SEQ ID No:8);

5' GAG AGC TCC CGA GGC AGA GAA CAG 3' (SEQ ID No:9);

5' GAG AGC TCC TGA GGC AGA GAA CAG 3' (SEQ ID No:10);

5' CTG TTC TCT GCC TCA GGA GCT CTC 3' (SEQ ID No:11); and

5' CTG TTC TCT ACC TCA GGA GCT CTC 3' (SEQ ID No: 12).

14. The method as in claim 12, wherein said step of determining an allelic pattern comprises digestion with at least one restriction enzyme selected from the group consisting of Ava I and Bsu36I.

15. A method of predicting a patient's increased risk of susceptibility to asthma, comprising the steps of:

(a) isolating genomic DNA from a patient;

(b) detecting a polymorphism at IL-1B (+3954) or at IL-1B (−511);

wherein the presence of allele 2 at the IL-1B (+3954) locus or the IL-1B (−511) locus is indicative of increased risk of susceptibility to asthma.

* * * * *